United States Patent [19]

Mitsumori et al.

[11] Patent Number: 5,055,469
[45] Date of Patent: Oct. 8, 1991

[54] QUATERNARY PYRIDINIUM SALTS USEFUL FOR ULCER TREATMENT

[75] Inventors: Naomichi Mitsumori, Kobe; Yasuhiro Nishimura, Fujiidera; Keiko Yokota, Nagoya; Shiro Okuno, Osaka; Motoko Suzuki, Ibaraki, all of Japan

[73] Assignee: Hamari Chamicals, Ltd., Osaka, Japan

[21] Appl. No.: 394,080

[22] Filed: Aug. 15, 1989

[30] Foreign Application Priority Data

Aug. 18, 1988 [JP] Japan ................................. 63-205465

[51] Int. Cl.$^5$ .................. A61K 31/495; A61K 31/44; C07D 401/10
[52] U.S. Cl. ................................. 514/252; 514/352; 514/354; 514/355; 514/357; 544/360; 544/365; 546/309; 546/316; 546/323; 546/337
[58] Field of Search ............... 546/337, 233, 234, 309, 546/316, 323, 337; 544/165, 360, 365; 514/357, 252, 352, 354, 357

[56] References Cited

U.S. PATENT DOCUMENTS 1,887,996 11/1932 Conzetti .............................. 546/337
4,233,055 11/1980 Martin ................................ 546/337

FOREIGN PATENT DOCUMENTS 771875 4/1957 United Kingdom ................ 544/165

Primary Examiner—Joseph Paul Brust
Assistant Examiner—Jacqueline Haley
Attorney, Agent, or Firm—Burgess, Ryan & Wayne

[57] ABSTRACT

There are provided quaternary ammonium compounds of the formula:

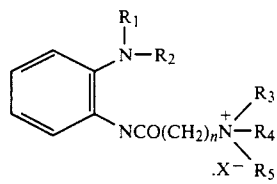

wherein $R_1$ and $R_2$, each independently represents a hydrogen atom, a $C_1$ to $C_8$ lower alkyl or alkenyl group, or $C_3$ to $C_8$ lower cycloalkyl, cycloalkenyl, aralkyl or aryl group; or $R_1$ and $R_2$ combine with each other in combination with the adjacent N and carbon atoms or further with at least one of nitrogen, oxygen and sulfur atoms to represent a 3- to 8- membered heterocyclic ring group: $R_3$, $R_4$ and $R_5$, each independently represents a $C_1$ to $C_8$ lower alkyl or alkenyl group, $C_3$ to $C_8$ lower cycloalkyl, cycloalkenyl, aralkyl or aryl group; or either two of $R_3$, $R_4$ and $R_5$ combine with each other in combination with the adjacent N and carbon atoms or further with at least one of nitrogen, oxygen and sulfur atoms to represent a 3- or 8-membered heterocyclic ring group, with the remaining being the same as defined in the above; or $R_3$, $R_4$ and $R_5$ combine with one another in combination with the adjacent N to represent a nitrogen-containing bicyclo ring or nitrogen-containing aromatic ring group: n is an integer of 1 to 8; and $x^-$ represents an anion being capable of forming a quaternary ammonium group.

The compounds are useful in treatment of ulcer in mammals.

13 Claims, No Drawings

QUATERNARY PYRIDINIUM SALTS USEFUL FOR ULCER TREATMENT

FIELD OF THE INVENTION

This invention relates to quaternary ammonium derivatives. The compounds of this invention show potent gastric-secretion suppressing activity and useful for treating gastric ulcer, duodenal ulcer and the like.

The compounds of this invention all possess heretofore unknown chemical structures. With reference to the anti-ulcer activity which the compounds of this invention demonstrate, there have conventionally been synthesized a great variety of chemical compounds, such as cimetidine, gefarnate and omeprazole.

BACKGROUND OF THE INVENTION

The drug substances, inclusive of the above-mentioned compounds, which have conventionally been employed for the treatment of gastric ulcer or duodenal ulcer, have several defects to be improved in terms of anti-ulcer activity, gastric-secretion suppressing activity and others.

The present inventors, with a specific view to finding a substance which exhibits improved anti-ulcer and gastric-secretion suppressing activities, conducted intensive research and as a result, have come to establish this invention.

SUMMARY OF THE INVENTION

The compound of this invention are those represented by the following formula (I):

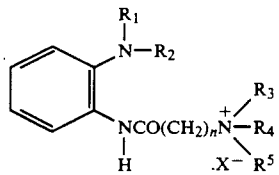

wherein $R_1$ and $R_2$, each independently represents a hydrogen atom, a $C_1$ to $C_8$ lower alkyl or alkenyl group, or $C_3$ to $C_8$ lower cycloalkyl, cycloalkenyl, aralkyl or aryl group; or $R_1$ and $R_2$ combine with each other in combination with the adjacent N and carbon atoms or further with at least one of nitrogen, oxygen and sulfur atoms to represent a 3- to 8-membered heterocyclic ring group: $R_3$, $R_4$ and $R_5$, each independently represents a $C_1$ to $C_8$ lower alkyl or alkenyl group, $C_3$ to $C_8$ lower cycloalkyl, cycloalkenyl, aralkyl or aryl group; or either two of $R_3$, $R_4$ and $R_5$ combine with each other in combination with the adjacent N and carbon atoms or further with at least one of nitrogen, oxygen and sulfur atoms to represent a 3- to 8-membered heterocyclic ring group, with the remaining being the same as defined in the above; or $R_3$, $R_4$ and $R_5$ combine with one another in combination with the adjacent N to represent a nitrogen-containing bicyclo ring or nitrogen-containing aromatic ring group: n is an integer of 1 to 8; and $X^-$ represents an anion being capable of forming a quaternary ammonium group.

DETAILED DESCRIPTION OF THE INVENTION

Referring to the general formula (I), Examples of the $C_1$ to $C_8$ lower alkyl or lower alkenyl group represented by $R_1$ or $R_2$ include methyl, ethyl, propyl, isopropyl, butyl, isobutyl, tert-butyl, pentyl, hexyl, octyl, allyl, 3-methyl-3-butenyl and the like. As the $C_3$ to $C_8$ lower cycloalkyl or cycloalkenyl group, there may be mentioned, for example, cyclopropyl, cyclobutyl, cyclopentyl, cyclohexyl, cyclooctyl, cyclopentenyl, cyclohexenyl, cyclooctenyl, etc. Examples of the aralkyl group include benzyl and substituted benzyl group, such as (2-methylphenyl)methyl, (3-methylphenyl)methyl, ((4-methylphenyl)methyl, (4-methoxyphenyl)methyl and (4-ethoxyphenyl)methyl, phenylethyl and substituted phenylethyl, such as (4-methylphenyl)ethyl, (4-methoxyphenyl)ethyl and (4-ethoxyphenyl)ethyl, and the like. Examples of the aryl group include phenyl, chlorophenyl, bromophenyl, methoxyphenyl, ethoxyphenyl, methylphenyl, ethylphenyl, propylphenyl, isopropylphenyl, butylphenyl, isobutylphenyl, trifluoromethylphenyl, nitrophenyl, aminophenyl, hydroxyphenyl, 4-methoxy-3-hydroxyphenyl, 4-hydroxy-3-methoxyphenyl, naphthyl, methoxynaphthyl, bromonaphthyl, chloronaphthyl, fluoronaphthyl, nitronaphthyl, aminonaphthyl, and the like. As the 3-membered to 8-membered heterocyclic ring group wherein $R_1$ and $R_2$ are combined each other in combination with the adjacent N and carbon atoms or further with at least one of nitrogen, oxygen and sulfur atoms, there may be mentioned, for example, aziridinyl, pyrrolyl, 3-pyrrolynyl, pyrrolidinyl, pyrazolyl, 2-pyrazolinyl, imidazolyl, piperidinyl, morpholinyl, thiomorpholinyl and the like.

Examples of the $C_1$ to $C_8$ lower alkyl or lower alkenyl group represented by $R_3$, $R_4$ and $R_5$ include methyl, ethyl, propyl, isopropyl, butyl, isobutyl, tert-butyl, pentyl, hexyl, octyl, allyl, 3-methy12-butenyl and the like.

Examples of the $C_3$ to $C_8$ lower cycloalkyl or cycloalkenyl group include cyclopropyl, cyclobutyl, cyclopentanyl, cyclohexyl, cyclooctyl, cyclopentenyl, cyclohexenyl, cycloheptenyl, cyclooctenyl and the like. As the aralkyl group, there may be mentioned, for example, benzyl and substituted benzyl groups, such as (2-methylphenyl)-methyl, (3-methylphenyl)methyl, (4-methylphenyl)-methyl, (4-methoxyphenyl)methyl and (4-ethoxyphenyl)methyl, phenylethyl and substituted phenylethyl groups such as (4-methylphenyl)ethyl, (4-methoxyphenyl)ethyl and (4-ethoxypheny)ethyl, while the examples of the aryl group include phenyl, chlorophenyl, bromophenyl, fluorophenyl, methoxyphenyl, ethoxyphenyl, methylphenyl, ethylphenyl, propylphenyl, isopropylphenyl, butylphenyl, isobutylphenyl, trifluoromethylphenyl, nitrophenyl, naphthyl, methoxynaphthyl, methylnaphthyl, bromonaphthyl, chloronaphthyl, fluoronaphthyl, nitronaphthyl and the like.

As the 3-membered to 8-membered haterocyclic ring group wherein either two of $R_3$, $R_4$ and $R_5$ combine with each other in combination with the adjacent N and carbon atoms or further with at least one of nitrogen, oxygen and sulfur atoms, there may be mentioned, for example, the same group as illustrated in the above for the heterocyclic ring group to be formed by $R_1$ and $R_2$.

Examples of the nitrogen-containing bicyclio ring group, wherein $R_3$, $R_4$ and $R_5$ combine one another through the carbon atom, include quinuclidinyl, 2-hydroxyquinuclidinyl, quinuclidinone-1-il and the like, while those of the nitrogen-containing aromatic ring group formed by $R_3$, $R_4$ and $R_5$ include residues, such as pyridine, picoline, chloropyridine, chloropicoline, hydroxypyridine, hydroxypicoline, hydroxycarbonylpyridine, carbamoylpyridine and hydrocarbonylpyridine.

Examples of the anion represented by $X^-$ include chlorine ion, bromine ion, fluorine ion, sulfuric acid ion, p-toluenesulfonic acid ion, methanesulfonic acid ion, formic acid ion, benzoic acid ion, tartaric acid ion, oxalic acid ion, maleic acid ion, fumaric acid ion, and the like.

The compound of this invention can be produced by the following procedures.

With reference to the first procedure, 2-substituted aminoanilline represented by the formula (II):

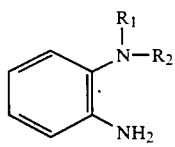 (II)

(wherein $R_1$ and $R_2$ are as defined in the above) is reacted with a reactive derivative of a carboxylic acid represented by the formula (III):

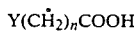 (III)

(wherein Y is halogene or an alkyl or allylsulfonyloxy group) to produce N-(2-substituted aminophenyl)carboxamide represented by the formula (IV):

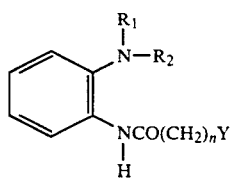 (IV)

(wherein $R_1$, $R_2$, Y and n are as defined in the above), followed by action of a tertiary amine represented by the formula (V):

 (V)

(wherein $R_3$, $R_4$ and $R_5$ are as defined in the above) to give the compound (I).

As the reactive derivative of the formula (III), there may be mentioned, for example, chloroacetyl chloride, bromoacetyl bromide, bromopropyl chloride and bromopropyl bromide.

The reaction of the compound of the formula (II) with the reactive derivative of the compound of the formula (III) is carried out, in the proportions in which 1 to 10 equivalents, preferably 1 to 2 equivalents, of the latter are used against the former, in an inert solvent (for example, chloroform, methylene chloride, ethylene dichloride, trichloroethylene, carbon tetrachloride, benzene, toluene, xylene, ethyl acetate, isobutyl acetate, n-butyl acetate, methyl ethyl ketone, acetone, dimethylformamide, dimethylsulfoxide, dimethylimidazolinone, hexaphosphoric amide, etc.) at a temperature of $-20°$ C. to the boiling point of solvent used, preferably 10° C. to 30° C. The reaction proceeds advantageously in the presence of 1 to 10 equivalents, preferably 1 to 2 equivalents, of a deacidifying agent. Examples of the deacidifying agent include organic or inorganic bases, such as triethylamine, pyridine, triisopropylamine, N-methylmorpholine, anhydrous sodium hydrogencarbonate, anhydrous sodium carbonate, anhydrous potassium hydrogencarbonate, anhydrous potassium carbonate, sodium hydroxide, potassium hydroxide, etc.

In this manner, the reaction between the compounds (II) and (III) produces the amide (IV).

The reaction of the amide (IV) with the tertiary amine (V) is conducted, in the proportions where 1 to 10 equivalents, preferably 1 to 5 equivalents, of the latter are used to the former, without utilizing solvent or in a inert solvent (for example, chloroform, methylene chloride, ethylene dichloride, trichloroethylene, carbon tetrachloride, benzene, toluene, xylene, ethyl acetate, isobutyl acetate, n-butyl acetate, methyl ethyl ketone, acetone, dimethylformamide, dimethylsulfoxide, dimethylimidazoline, hexaphosphoric amide, etc.) at a temperature of $-20°$ C. to 200° C., preferably room temperature to 120° C. A pressure container, such as a sealed tube, may be used in the reaction, as the case may be.

In the second procedure, a carboxylic acid or its ester represented by the formula (VI):

(wherein $R_6$ is a hydrogen atom or $C_1$ to $C_8$ lower alkyl group; and Y and n are as defined in the above) is reacted with a tertiary amine represented by the formula (V):

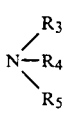 (V)

(wherein $R_3$, $R_4$ and $R_5$ are as defined in the above) to give a carboxylic acid derivative represented by the formula (VII):

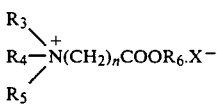 (VII)

(wherein $R_3$, $R_4$, $R_5$, $R_6$ and $X^-$ are as defined in the above), and the carboxylic acid derivative, after its $COOR_6$ group is derived into a reactive group of the carboxylic group, if necessary, is reacted with 2-substituted aminoaniline represented by the formula:

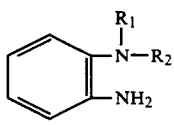 (VIII)

(wherein $R_1$ and $R_2$ are as defined in the above) to produce the compound (I).

Examples of the halogenocarboxylic acid or its ester represented by the formula (VI) include 2-chloroacetic acid, 3-chloropropionic acid, 4-chlorobutyric acid and their methyl and ethyl esters.

The reaction of the compound (VI) with the tertiary amine (V) is carried out in an inert solvent (for example, chloroform, methylene chloride, ethylene dichloride, trichloroethylene, carbon tetrachloride, benzene, toluene, xylene, ethyl acetate, isobutyl acetate, n-butyl acetate, methyl ethyl ketone, acetone, dimethylforamide, dimethylsulfoxide, dimethylimidazolinone, hexaphosphoric amide, etc.) at a temperature of −20° C. to 200° C., preferably room temperature to 120° C. In this manner, there can be produced the quaternary ammonium carboxylic acid derivative (VII), which is then reacted with the 2-substituted aminoaniline (VIII) after, or directly without, being derived into a reactive derivative in the carboxyl group (for example, acid chloride, acid anhydride, mixed acid anhydride, active esters such as p-nitrophenyl ester, etc.). This reaction is conducted in an inert solvent or without solvent, under cooling or heating. For example, the reaction is desirably carried out at −20° C. to room temperature in the case of the compound (VII) being a reactive derivative such as acid chloride, active ester and acid anhydride, and at 100° C. to 200° C. in cases where the compound (VII) is used as such.

Referring now to the third procedure, an amide compound of the formula (IX):

$$Y(CH_2)_nCONH_2 \qquad (IX)$$

(wherein Y and n are as defined in the above) is reacted with a tertiary amine represented by the formula (V):

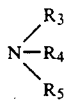

(V)

(wherein $R_3$, $R_4$ and $R_5$ are as defined in the above) to give an amide derivative represented by the formula (X):

(X)

(wherein $R_3$, $R_4$ and $R_5$, X and n are as defined in the above), which is then reacted with 2-halogeno-N-substituted aniline represented by the formula (XI):

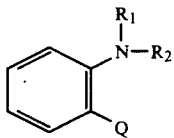

(XI)

(wherein $R_1$ and $R_2$ are as defined in the above; and Q is a halogen atom) to produce the compound (I).

As the amide compound of the formula (IX), there may be mentioned, for example, 2-dichloroacetamide and 3-bromopropionamide.

The reaction of the compound (IX) with the tertiary amine (V) is carried out in an inert solvent (for example, chloroform, methylene chloride, ethylene dichloride, trichloroethylene, carbon tetrachloride, benzene, toluene, xylene, ethyl acetate, isobutyl acetate, n-butyl acetate, methyl ethyl ketone, acetone, dimethylformamide, dimethylsulfoxide, dimethylimidazoline, hexaphosphoric amide, etc.) at a temperature of −20° C. to 200° C., preferably room temperature to 120° C. In this manner, the amide derivative (X) is produced.

Then, the compound (X) is reacted with the 2-halogeno-N-substituted aniline (XI). The reaction is conducted in an inert solvent (for example, benzene, toluene, xylene, ethyl acetate, isobutyl acetate, n-butyl acetate, methyl ethyl ketone, acetone, dimethylformamide, dimethylsulfoxide, dimethylimidazoline, hexaphosphoric amide, etc.) at a temperature of 50° C. to 300° C., preferably 50° C. to 200° C., whereby the reaction can be allowed to proceed in the presence or absence of a base (for example, anhydrous potassium carbonate, anhydrous potassium hydrogencarbonate, anhydrous sodium carbonate, anhydrous sodium hydrogencarbonate, etc.) and a catalyst (for example, copper powder, copper carbonate, cuprous iodide, cuprous chloride, etc.). In this manner, the compound (I) is obtained.

As the compound of this invention as represented by the formula (I), there may be mentioned, for example:

1-[2-[[2-[(4-Methylphenyl)amino]phenyl]amino]-2-oxoethyl]-pyridinium chloride,
4-Acetylamino-1-[2-oxo-2[[2-(phenylamino)phenyl]amino]ethyl]-pyridinium chloride,
3-Carbamoyl-1-[2-oxo-2-[[2-(phenylamino)phenyl]amino]ethyl]-pyridinium chloride,
1-[2-Oxo-2-[[2-[(phenylmethyl)amino]pnenyl]amino]ethyl]-pyridinium chloride,
1-[2-Oxo-2 [2-[(phenylmethyl)amino]phenyl]amino]ethyl]-pyridinium bromide,
1-[2-oxo-[[2-(phenylamino)phenyl]amino]ethyl]-pyridinium oxalate,
2-Methyl-1-[2-oxo-2-[[2-(phenylamino)phenyl]amino]ethyl]-pyridinium chloride,
4-Methyl-1-[2-oxo-2-[[2-(phenylamino)phenyl]amino]ethyl]-pyridinium chloride,
4-Chloro-1-[2-oxo-2-[[2-(phenylamino)phenyl]amino]ethyl]-pyridinium chloride,
4-Chloro-1-[2-oxo-2-[[2-(phenylamino)phenyl]amino]ethyl]-pyridinium chloride,
4-Chloro-2-methyl-1-[2-[[2-[(4-methylphenyl)amino]phenyl]-amino]-2-oxoethyl]pyridinium chloride,
1-[2-[[2-(Cyclopropylamino)phenyl]amino]-2-oxoethyl]-pyridinium chloride,
1-[2-[[2-(Cyclopropenylamino)phenyl]amino]-oxoethyl]-pyridinium chloride,
1-[2-[[2-(Cyclohexylamino)phenyl]amino]-2-oxoethyl]-pyridinium chloride,
1-[2-[[2-(Cyclohexenylamino)phenyl]amino]-2-oxoethyl]-pyridinium chloride,
1-[2-[[-(Ethylamino)phenyl]amino]-2-oxoethyl]-pyridinium chloride,
2-Oxo-2-[[2-(phenylamino)phenyl]amino]-N,N,N-triethylethanaminium chloride,
1-[2-[[2-[(4-Methylphenyl)amino]phenyl]amino]-2-oxoethyl]-quinuclidinium chloride,
N-Methyl-N-[2-oxo-2-[[2-(phenylamino)phenyl]amino]ethyl]-morphorinium chloride,
N,N-Dimethyl-N-[2-oxo-[[(phenylamino)phenyl]amino]ethyl]benzenaminium chloride,
N,N-Diethyl-N-[2-oxo-2-[[(phenylamino)phenyl]amino]ethyl]-benzenaminium chloride,
N,N-Dimethyl-4-methyl-N-[2-oxo-2-[[(phenylamino)phenyl]-amino]ethyl]benzenaminium chloride,
N,N-Dimethyl-4-methyl-N-[2-oxo-2-[[(phenylamino)phenyl]-amino]ethyl]benzenaminium bromide.
N,N-Dimethyl-N-[2-oxo-2-[[(phenylamino)phenyl]amino]ethyl]-benzenemethanaminium chloride,
N,N-Diisopropyl-N-[2-oxo-2-[2-(phenylamino)phenyl]amino]ethyl]-benzenemethanaminium bromide,
N,N-Diisopropyl-N-[2-oxo-2-[[2-(phenylamino)phenyl]amino]-ethyl]benzenemethanaminium chloride,
5-Methyl-1-[2-oxo-2-[[2-(phenylamino)phenyl]amino]ethyl]imidazolinium chloride, 5-Methyl-3-[2-oxo-2[[2-(phenylamino)phenyl]amino]ethyl]-thiazolinium chloride, 5-Hydroxyethyl-4-methyl-3-[2-oxo-2-[[2-(phenylamino)phenyl]amino]ethyl]thiazolinium chloride 3-Methyl-1-[2-oxo-2-[[2-[(phenylmethyl)amino]phenyl]amino]-ethyl]imidazolinium chloride, 1-[2-Oxo-2-[[2-(piperazin-1-yl)phenyl]amino]ethyl]-pyridinium chloride, and the like.

The compounds of this invention are usable orally in the dosage forms of tablets, capsules, granules and powders, and parenterally in the dosage forms of injectable solutions and suppositories. The above pharmaceutical preparations, if necessary, may be incorporated with ordinarily used additives, such as auxiliary agents, stabilizers, wetting agents, emulsifying agents and buffer solutions. With reference to the dosage amounts, the compounds of this invention are normally employed orally in the doses of 10 mg to 1 g per day, but the dose range is not understood to be limited, being variable depending upon the treatment. Also, it is possible to use the compounds in combination with other drugs in accordance with the type of diseases and the treatment.

Below described are the examples to illustrate this invention, but this invention shall not be limited by the examples.

Example 1

Synthesis of 2-oxo-2-[[2-(phenylamino)phenyl]amino]-N,N,N-triethylethanaminium chloride Dissolved in 30 ml of triethylamine is 6.2 g of 2-chloro-N-[2-(phenylamino)phenyl]acetamide, and the solution is heated under reflux for 2 hours. As the reaction proceeds, the precipitates separate out. After completion of the reaction, the reaction mixture is cooled and stirred for 3 hours while keeping the inside temperature at 5° C. to 10° C. The precipitates which separate out are recovered by filtration, and recrystallized from a small amount of chloroform to give 3.1 g of 2-oxo-2-[[2-phehylamino)phenyl]-amino]-N,N,N-triethylethanaminium chloride showing a melting point of 90° C. to 100° C.

IR (KBr, cm$^{-1}$): 3390, 1675, 1650, 1515

NMR (DMSO-d$_6$, ppm): 1.26(t,9H), 3.46(q,8H), 4.37(s,2H), 6.06 to 7.30(m,7H), 7.52(d,1H), 8.02(s,1H), 10.61(s,1H).

Example 2

Synthesis of 1-[2-[[2-[(4-methylphenyl)amino]-phenyl]-amino]-2-oxoethyl]quinuclidinium chloride Dissolved in 10 ml of 2-butanone are 6.2 g of 2-chloro-N-[2-[(4-methylphenyl)amino]phenylacetamide and 3.3 g of quinuclidine, followed by refluxing for 2 hours. After completion of the reaction, the reaction mixture is held at 5°° C. to 10° C. and left on standing at the same temperature for 5 hours, and recrystallized from ethanol to give the desired compound off 1-[2-[[-[(4-methylphenyl)amino]phenyl]amino]-2-oxoethyl]-quinuclidinium chloride.

Melting point: 236° C. to 238° C.

IR (KBr, cm$^{-1}$): 3240, 3180, 3110, 3975, 1680, 1610, 1590, 1580

NMR (DMSO-d6, ppm): 1.85(m,6H), 2.16(s,3H), 3.56 to 3.80 (m,6H), 4.28(s,2H), 6.60 to 7.52(m,8H), 7.80(s,1H), 0.64(s,iH)

Example 3

Synthesis of N-methyl-N-[2-oxo-2-[[2-(phenylamino)-phenyl]amino]ethyl]morphorinium chloride Following the same procedure as described in Example 1 except the use of N-methylmorpholine in place of triethylamine, there is obtained N-methyl-N-[2-oxo-2-[[2-(phenylamino)phenyl]amino]ethyl]morpholinium chloride.

Melting point: 170° C. to 173° C.

IR (KBr, cm$^{-1}$): 3260, 3200, 3120, 1695, 1620, 1590, 1555, 1520.

NMR (DMSO-d$_6$, ppm): 3.40(s,3H), 3.61(m,4H), 3.92(m,4H), 4.71(s,2H), 6.55 to 7.31(m,9H), 7.52(d,1H), 8.04(s,1H), 10.77(s,1H).

Example 4

Synthesis of 1-[2-[[2-[(4-methylphenyl)amino]phenyl]-amino]-2-oxoethyl]pyridinium chloride By the same manner as described in Example 1 except for employing pyridine in place of triethylamine, there is obtained 1-[2-[[2-[(4-methylphenyl)amino]phenyl]amino]-2-oxoethyl]pyridinium chloride. The compound, when recrystallized from methanol, shows a melting point of 221° C. to 230° C.

IR (KBr, cm.$^{-1}$): 3225, 1680, 1640, 1605, 1540, 1515

NMR (dmso-d$_6$, ppm): 2.20(s,3H), 5.82(s,2H), 6.60 to 7.50 (m,8H), 7.96 to 8.16(m,3H), 8.44 to 8.62(m,1H), 9.06(t,2H), 10.64(s,1H).

Example 5

Synthesis of 4-acetylamino-1-[2-oxo-2-[[2-(phenylamino)phenyl]amino]ethyl]pyridinium chloride Dissolved in 30 ml of chloroform are 6.2 g of 2-chloro-N-[2-(phenylamino)phenyl]acetamide and 5.0 g of 4-acetylaminopyridine, and the solution is left on standing overnight. After completion of the reaction, the reaction mixture is held at 5° C. to 10° C., and left on standing at the same temperature for 5 hours. The precipitates, which separate out, are recovered by filtration and recrystallized from ethanol to give the desired compound of 4-acetylamino-1-[2-oxo-2-[[2-(phenylamino)-phenyl]amino]ethyl]pyridinium chloride.

Melting point: 236° C. to 239° C.

IR (KBr, cm.$^{-1}$): 3300, 1715, 1680, 1640, 1590

NMR (DMSO-d$_6$, ppm): 2.21(s,3H), 5.48(s,2H), 6.60 to 7.28(m,10H), 7.44(d,1H), 7.88(s,1H), 8.06(d,2H), 8.64(d,2H), 10.36(s,1H).

Example 6

Synthesis of 3-carbamoyl-1-[2-oxo-2-[[2-(phenylamino)phenyl]amino]ethyl]pyridinium chloride By substantially the same manner as described in Example1 5 except for employing nicotinamide in place of 4-acetylaminopyridine, there is synthesized 3-carbamoyl-1-[2-oxo-2-[[2-(phenylamino)phenyl]amino]ethyl]pyridinium chloride.

Melting point: 233° C. to 236° C. 3-carbamoyl-pyridinium chloride.

Melting point: 233° C. to 236° C.

IR (KBr, cm$^{-1}$): 3350, 3275, 1690, 1675, 1615, 1590.

NMR (DMSO-d, ppm): 5.88(s,2H), 6.60 to 7.28(m,9H), 8.00 to 9.20(m,7H), 9.52(m,1H), 10.52(s,1H).

Example 7

Synthesis of 1-{2-[2-(piperazine-1-yl)phenyl]amino-2-oxoethyl} pyridinium chloride By following substantially the same procedure as described in Example 1, there can be synthesized 1-{2-[2-(piperazine-1-yl)phenyl]amino-2-oxoethyl} pyridinium chloride.

IR (KBr, cm$^{-1}$): 3150, 1680, 1630, 1600, 1575, 1515, 1500

NMR (DMSO-d$_6$, ppm): 1.44 to 1.92(m,6H), 2.78(m,4H), 5.89 (s,2H), 6.80 to 7.12(m,4H), 7.70(d,1H), 8.12(t,2H), 8.56 (t,1H, 9.10(d,2H), 9.56(s,1H)

Example 8

The compound of Example 4 was determined for antiulcer activity by means of the following procedure:

Water-immersion stress ulceration method

Male Slc:SD rats (7-weeks aged: divided in groups each consisting of 6 to 8 animals), after being fasted for 24 hours, were placed in stress cages and immersed in water at 23° C. up to the xyphoid process. After stress loading for 7 hours, the rats were killed through exsanguination, and the stomachs were removed, perfused in the inside with 10 ml of 2% formalin and then immersed in the same solution for 10 minutes for fixation. The stomachs were incised along the greater curvature, and the ulcers thus induced were measured for length under the stereoscopic microscope (magnification×10), whereby the total sum of the lengths was taken as an ulcer index (U.I., in mm). The test substance was given orally to rats in the form of a 4% gum arabic suspension 30 minutes before stress loading. The results are shown in Table 1.

Acute toxicity

A group of five male ddY mice (4-weeks aged) was used for testing.

The compound of Example 4 was suspended in 4% gum arabic solution to prepare a test pharmaceutical, which was given orally to each test animal once.

The test animals were observed for 7 days, and the LD$_{50}$ values were calculated to determine the acute toxicity. The results are shown in Table 2.

TABLE 1

| Treatment | Dose mg/kg | U.I. Mean ± S.E. | Inhibition rate, % |
| --- | --- | --- | --- |
| Non-treated control | | 13.4 ± 2.71 | |
| Test substance | 10 | 10.8 ± 3.15 | 19.0 |
| | 30 | 3.3 ± 1.82 | 75.1* |
| | 100 | 1.3 ± 0.88 | 90.0** |
| Cimetidine | 30 | 5.2 ± 3.40 | 61.4 |

Note,
*p < 0.05,
**p < 0.01

TABLE 2

| Test substance | LD$_{50}$ value |
| --- | --- |
| Compound of Example 4 | Not less than 2000 mg/kg |

As may be evident from the above toxicity data, the compounds of this invention exhibit an extremely low degree of acute toxicity, and are adequately suitable for the use as a drug.

This invention can provide the novel quaternary ammonium compounds being capable of affording the pharmaceutically effective treatment means against gastric and duodenal ulcers.

We claim:

1. A compound of the formula:

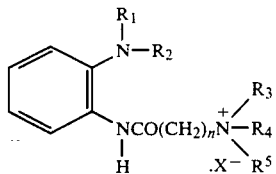

wherein (1) $R_1$ and $R_2$, each independently represents a hydrogen atom or a $C_1$ to $C_8$ alkyl group, or (2) one of $R_1$ and $R_2$ represents a hydrogen atom and the other represents a $C_3$ to $C_6$ cycloalkyl or cycloalkenyl group, a benzyl group which may be substituted with methyl, methoxy or ethoxy; or a phenyl group which may be substituted with a halogen atom, a $C_1$ to $C_2$ alkoxy group, a $C_1$ to $C_4$ alkyl group, trifluoromethyl, nitro, amino or hydroxy group; or (3) $R_1$ and $R_2$ combine with each other in combination with the adjacent N to represent a piperazine ring: $R_3$, $R_4$, $R_5$ and the adjacent N are incorporated together to represent a pyridine ring which may be substituted with a halogen atom, methyl, acetylamino or carbamoyl group: n is 1: and $X^-$ represents an anion capable of forming a quaternary ammonium group.

2. A compound according to claim 1, wherein one of $R_1$ and $R_2$ is a hydrogen atom and the other is a phenyl group which may be substituted with a halogen atom, a $C_1$ to $C_2$ alkoxy group, a $C_1$ to $C_4$ alkyl group, trifluoromethyl, nitro, amino or hydroxy group.

3. A compound selected from the group consisting of
2-methyl-1-[2-oxo-2-[[2-(phenylamino)phenyl]amino]ethyl]-pyridinium chloride,
4-methyl-1-[2-oxo-2-[[2-(phenylamino)phenyl]amino]ethyl]-pyridinium chloride,
4-chloro-1-[2-oxo-2-[[2-(phenylamino)phenyl]amino]ethyl]-pyridinium chloride,
1-[2-[[2-[(4-methylphenyl)amino]phenyl ]amino]-2-oxoethyl]-pyridinium chloride,
1-[2-oxo-2-[[2-[(phenylmethyl)amino]phenyl]amino]ethyl]-pyridinium chloride, and
1-[2-oxo-2-[[2-[(phenylmethyl)amino]phenyl]amino]ethyl]-pyridinium bromide.

4. A compound according to claim 3, which is 2-methyl-1-[2-oxo-2-[[2-(phenylamino)phenyl]amino]ethyl]-pyridinium chloride.

5. A compound according to claim 3, which is 4-methyl-1-[2-oxo-2-[[2-(phenylamino)phenyl]amino]ethyl]-pyridinium chloride.

6. A compound according to claim 3, which is 4-chloro-1-[2-oxo-2-[[2-(phenylamino)phenyl]amino]ethyl]-pyridinium chloride.

7. A compound according to claim 3, which is 1-[2-[[2-[(4-methylphenyl)amino]phenyl]amino]-2-oxoethyl]-pyridinium chloride.

8. A compound according to claim 3, which is 1-[2-oxo-2-[[2-[(phenylmethyl)amino]phenyl]amino]ethyl]-pyridinium chloride.

9. A compound according to claim 3, which is 1-[2-oxo-2-[[2-[(phenylmethyl)amino]phenyl]amino]ethyl]-pyridinium bromide.

10. A pharmaceutical composition comprising a therapeutically effective amount of a compound according to claim 1 in association with a pharmaceutical carrier or diluent.

11. A method of treating ulcer in a mammal which comprises administering a therapeutically effective amount of a compound according to claim 1 to a mammal in need of such treatment.

12. A method according to claim 11 comprising administering the compound orally to said mammal.

13. A method according to claim 11 comprising administering said compound in an amount of from 10 mg. to 1 g. per day to said mammal.

* * * * *